(12) United States Patent
Kawaguchi et al.

(10) Patent No.: US 8,530,711 B2
(45) Date of Patent: Sep. 10, 2013

(54) PROCESS FOR PRODUCING 2,3,3,3-TETRAFLUOROPROPENE

(75) Inventors: Satoshi Kawaguchi, Tokyo (JP); Hidekazu Okamoto, Tokyo (JP); Yu Takeuchi, Tokyo (JP); Hirokazu Takagi, Tokyo (JP); Kunio Watanabe, Tokyo (JP); Koichi Yanase, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 13/167,254

(22) Filed: Jun. 23, 2011

(65) Prior Publication Data

US 2011/0319677 A1     Dec. 29, 2011

Related U.S. Application Data

(60) Provisional application No. 61/365,582, filed on Jul. 19, 2010.

(30) Foreign Application Priority Data

Jun. 23, 2010  (JP) ................................. 2010-142669

(51) Int. Cl.
  *C07C 19/08*  (2006.01)
(52) U.S. Cl.
  USPC ......................................................... 570/176
(58) Field of Classification Search
  None
  See application file for complete search history.

(56) References Cited

U.S. PATENT DOCUMENTS

| | | | |
|---|---|---|---|
| 2,931,840 A * | 4/1960 | Marquis ........................ | 570/159 |
| 5,714,654 A | 2/1998 | Yamamoto et al. | |
| 2010/0022808 A1 | 1/2010 | Rao et al. | |

FOREIGN PATENT DOCUMENTS

| | | |
|---|---|---|
| EP | 396974 A1 * | 11/1990 |
| JP | 63-211245 | 9/1988 |
| JP | 8-193039 | 7/1996 |
| JP | 2003-176243 | 6/2003 |
| JP | 2010-510221 | 4/2010 |
| WO | WO 2009/035130 A2 | 3/2009 |
| WO | WO 2010/013576 A1 | 2/2010 |

OTHER PUBLICATIONS

U.S. Appl. No. 13/167,464, filed Jun. 23, 2011, Takagi, et al.
U.S. Appl. No. 13/167,455, filed Jun. 23, 2011, Okamoto.
U.S. Appl. No. 13/167,285, filed Jun. 23, 2011, Seki, et al.
U.S. Appl. No. 13/167,235, filed Jun. 23, 2011, Kawaguchi, et al.
U.S. Appl. No. 13/167,509, filed Jun. 23, 2011, Kawaguchi, et al.
U.S. Appl. No. 13/167,145, filed Jun. 23, 2011, Takagi, et al.
International Search Report issued Jul. 19, 2011 in PCT/JP2011/064428 (with English translation of category of cited documents).

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

The object is to provide a process for producing highly pure 2,3,3,3-tetrafluoropropene, whereby formation of 3,3,3-trifluoropropene is suppressed.

A process for producing 2,3,3,3-tetrafluoropropene, which comprises reacting a raw material compound composed of 1,1-dichloro-2,3,3,3-tetrafluoropropene and/or 1-chloro-2,3,3,3-tetrafluoropropene, and hydrogen in a gas phase in a reactor having a catalyst layer packed with a catalyst-supporting carrier, while maintaining the maximum temperature of the catalyst layer to be at most 130° C., to obtain formed gas containing 2,3,3,3-tetrafluoropropene, and then, contacting the formed gas discharged from the reactor, with alkali at a temperature of at most 100° C.

14 Claims, 1 Drawing Sheet

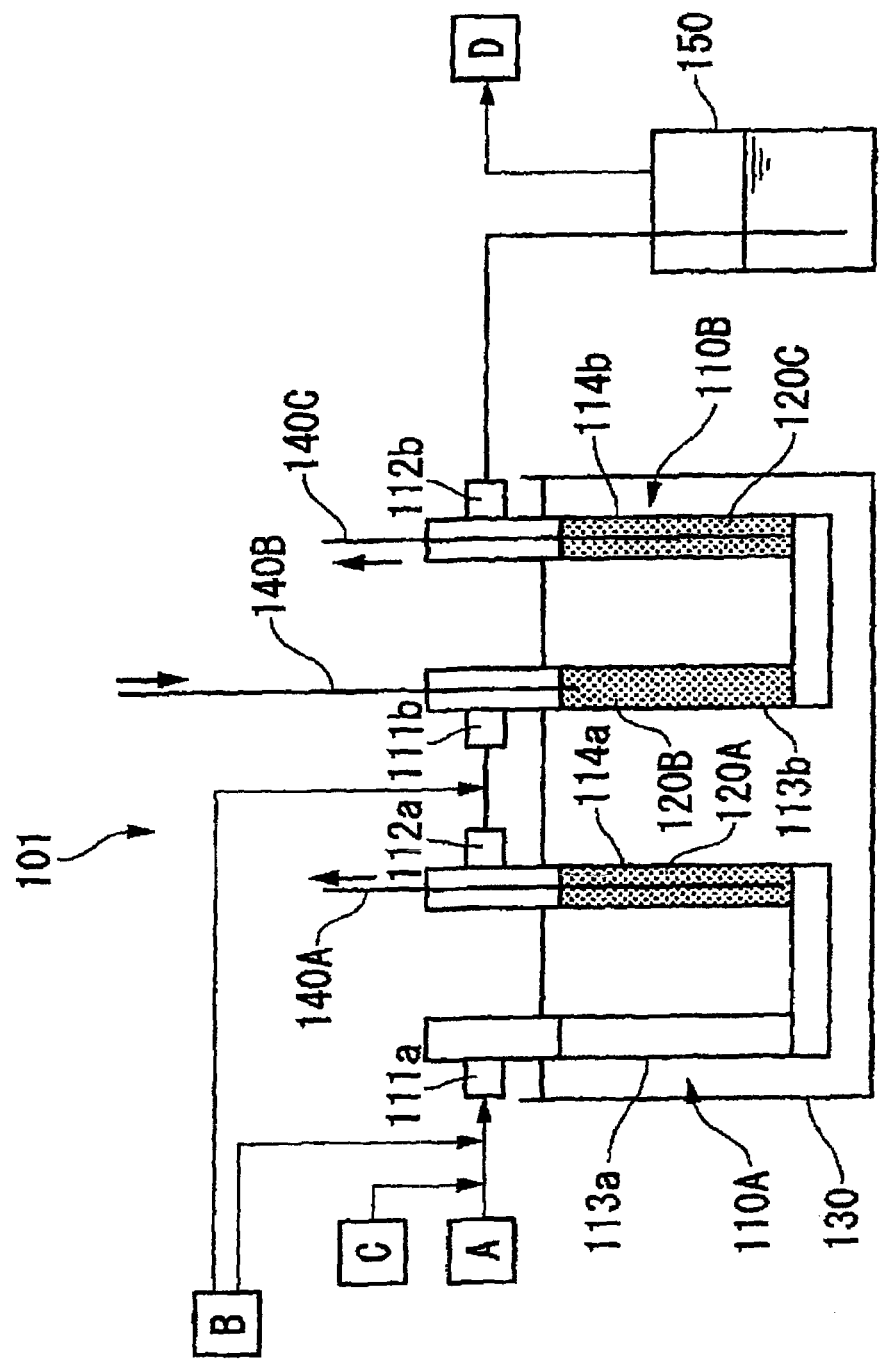

PROCESS FOR PRODUCING 2,3,3,3-TETRAFLUOROPROPENE

TECHNICAL FIELD

The present invention relates to a process for producing 2,3,3,3-tetrafluoropropene.

BACKGROUND ART 2,3,3,3-tetrafluoropropene ($CF_3CF=CH_2$, HFO-1234yf) is expected to be a new refrigerant which is less influential over the environment.

As a process for producing HFO-1234yf, a process has, for example, been proposed wherein 1,1-dichloro-2,3,3,3-tetrafluoropropene ($CF_3CF=CCl_2$, CFO-1214ya) and hydrogen gas are reached at a temperature of from 100 to 400° C., preferably from 125 to 350° C., in the presence of a catalyst having palladium supported on alumina (Patent Document 1).

$$CF_3CF=CCl_2+2H_2 \rightarrow CF_3CF=CH_2+2HCl \quad (1)$$

In the reaction of the formula (1), a large amount of hydrogen chloride is generated, and it is usual to neutralize and remove the hydrogen chloride by blowing, into an alkali aqueous solution, the formed gas containing HFO-1234yf and hydrogen chloride, discharged from the reactor.

However, in the reaction of the formula (1), 1,1,1,2-tetrafluoropropane ($CF_3CHFCH_3$, HFC-254eb) is formed as a byproduct, and when the formed gas is blown into an alkali aqueous solution, a dehydrofluorination reaction of HFC-254eb may take place by the alkali serving as a catalyst, to form 3,3,3-trifluoropropene ($CF_3CH=CH_2$, HFO-1243zf). HFO-1243zf has a boiling point close to HFO-1234yf and therefore cannot be separated therefrom by the subsequent distillation. Therefore, in HFO-1234yf as the product obtained by distillation, HFO-1243zf remains as an impurity, thus leading to deterioration of the quality of HFO-1234yf.

PRIOR ART DOCUMENT

Patent Document

Patent Document 1: WO2008/060614

DISCLOSURE OF INVENTION

Technical Problem

It is an object of the present invention to provide a process for producing highly pure 2,3,3,3-tetrafluoropropene, whereby formation of 3,3,3-trifluoropropene is suppressed.

Solution to Problem

The process for producing 2,3,3,3-tetrafluoropropene of the present invention comprises reacting a raw material compound composed of 1,1-dichloro-2,3,3,3-tetrafluoropropene and/or 1-chloro-2,3,3,3-tetrafluoropropene, and hydrogen in a gas phase in a reactor having a catalyst layer packed with a catalyst-supporting carrier, while maintaining the maximum temperature of the catalyst layer to be at most 130° C., to obtain formed gas containing 2,3,3,3-tetrafluoropropene, and then, contacting the formed gas discharged from the reactor, with water.

Further, the process for producing 2,3,3,3-tetrafluoropropene of the present invention comprises reacting a raw material compound composed of 1,1-dichloro-2,3,3,3-tetrafluoropropene and/or 1-chloro-2,3,3,3-tetrafluoropropene, and hydrogen in a gas phase in a reactor having a catalyst layer packed with a catalyst-supporting carrier, while maintaining the maximum temperature of the catalyst layer to be at most 130° C., to obtain formed gas containing 2,3,3,3-tetrafluoropropene, and then, contacting the formed gas discharged from the reactor, with alkali, while the temperature of the formed gas is adjusted to be at most 100° C. immediately before the contact with the alkali.

The above alkali is preferably an alkali aqueous solution.

Such an alkali aqueous solution is preferably an aqueous solution of at least one metal hydroxide selected from the group consisting of sodium hydroxide, potassium hydroxide and calcium hydroxide.

The concentration of such a metal hydroxide is preferably from 0.01 to 40 mass % in the alkali aqueous solution (100 mass %).

The catalyst is preferably palladium.

The carrier is preferably active carbon.

The packed density of the catalyst-supporting carrier in the catalyst layer is preferably from 0.5 to 1 g/cm³.

Advantageous Effect of Invention

According to the process for producing 2,3,3,3-tetrafluoropropene of the present invention, formation of 3,3,3-trifluoropropene is suppressed, and it is possible to obtain highly pure 2,3,3,3-tetrafluoropropene.

BRIEF DESCRIPTION OF DRAWING

FIG. 1 is a schematic view illustrating a reaction apparatus used in Examples.

DESCRIPTION OF EMBODIMENT

The process for producing 2,3,3,3-tetrafluoropropene ($CF_3CF=CH_2$, HFO-1234yf) of the present invention is the following process (a) or process (b).

(a) A process which comprises reacting a raw material compound composed of 1,1-dichloro-2,3,3,3-tetrafluoropropene ($CF_3CF=CCl_2$, CFO-1214ya) and/or 1-chloro-2,3,3,3-tetrafluoropropene ($CF_3CF=CHCl$, HCFO-1224yd), and hydrogen in a gas phase, in a reactor having a catalyst layer packed with a catalyst-supporting carrier, while maintaining the maximum temperature of the catalyst layer to be at most 130° C., to obtain formed gas containing HFO-1234yf, and then, contacting the formed gas discharged from the reactor, with water.

(b) A process which comprises reacting a raw material compound composed of CFO-1214ya and/or HCFO-1224yd, and hydrogen in a gas phase, in a reactor having a catalyst layer packed with a catalyst-supporting carrier, while maintaining the maximum temperature of the catalyst layer to be at most 130° C., to obtain formed gas containing HFO-1234yf, and then, contacting the formed gas discharged from the reactor with alkali at a temperature of at most 100° C.

The reaction of CFO-1213ya with hydrogen and the reaction of HCFO-1224yd with hydrogen are reactions which are represented by the following formulae.

$$CF_3CF=CCl_2+2H_2 \rightarrow CF_3CF=CH_2+2HCl \quad (1)$$

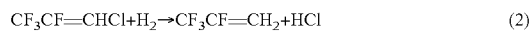

$$CF_3CF=CHCl+H_2 \rightarrow CF_3CF=CH_2+HCl \quad (2)$$

Firstly, the production of formed gas in the method (a) and the method (b) will be described. In these methods, the raw material compound composed of CFO-1214ya and/or HCFO-1224yd, and hydrogen, are reacted in a gas phase in a reactor having a catalyst layer packed with a catalyst-supporting carrier, while maintaining the maximum temperature of the catalyst layer to be at most 130° C., to obtain formed gas containing HFO-1234yf.

(Reactor)

As the reactor, a known reactor capable of forming a catalyst layer having a catalyst-supporting carrier packed, may be mentioned.

As the material for the reactor, glass, iron, nickel or an alloy containing iron or nickel as the main component may, for example, be mentioned.

The pressure in the reactor is preferably atmospheric pressure from the viewpoint of the operation efficiency.

(Catalyst and Catalyst-Supporting Carrier)

The catalyst is preferably a palladium catalyst, and the palladium catalyst is preferably employed as supported on a carrier. The palladium catalyst may be not only a palladium simple substance but also a palladium alloy. Otherwise, it may be a mixture of palladium with another metal, or a composite catalyst having palladium and another metal separately supported on carriers. The palladium alloy catalyst may, for example, be a palladium/platinum alloy catalyst or a palladium/rhodium alloy catalyst.

As the catalyst, a catalyst having only palladium or a palladium alloy supported on a carrier, or a catalyst having palladium and a metal other than palladium supported on a carrier, is preferred. The catalyst having palladium and metal other than palladium supported on a carrier tends to have a higher durability of the catalyst than the catalyst having only palladium supported on a carrier.

Other metals may, for example, be a Group 8 element (such as iron, ruthenium or osmium), a Group 9 element (such as cobalt, rhodium or iridium), a Group 10 element (such as nickel or platinum), gold, etc. Such other metals may be used alone, or two or more of them may be used in combination.

The proportion of other metals is preferably from 0.01 to 50 parts by mass, per 100 parts by mass of palladium.

As the carrier, active carbon or a metal oxide (such as alumina, zirconia or silica) may, for example, be mentioned, and active carbon is preferred from the viewpoint of the activity, durability and reaction selectivity.

As the active carbon, one obtained from e.g. a plant material (such as wood, charcoal, fruit shell, coconut shell or the like) or a mineral material (such as peat, lignite, coal or the like) may, for example, be mentioned. From the viewpoint of the durability of the catalyst, one obtained from a plant material is preferred, and coconut shell active carbon is particularly preferred. As the shape of the active carbon, briquette having a length of from 2 to 10 m, pulverized coal of from 4 to 50 mesh or granular coal may, for example, be mentioned. From the viewpoint of the activity, pulverized coal of from 4 to 20 mesh, or briquette having a length of from 2 to 5 mm is preferred.

The supported amount of palladium is preferably from 0.1 to 10 parts by mass, more preferably from 0.5 to 1 part by mass, per 100 parts by mass of the active carbon. When the supported amount of palladium is at least 0.1 part by mass, the conversion of the raw material compound and the hydrogen will be improved. When the supported amount of palladium is at most 10 parts by mass, an excessive temperature rise of the catalyst layer due to a heat of reaction can easily be suppressed, and formation of byproducts can easily be suppressed. Also in the case of a carrier other than active carbon, the supported amount of palladium is preferably the same amount as in the case of the above active carbon.

(Catalyst Layer)

By packing the catalyst-supporting carrier in a reactor, a catalyst layer is formed in the reactor. The packed density of the catalyst-supporting carrier in the catalyst layer is preferably from 0.5 to 1 g/cm$^3$, more preferably from 0.6 to 0.8 g/cm$^3$. When the packed density of the catalyst-supporting carrier is at least 0.5 g/cm$^3$, the packed amount of the catalyst-supporting carrier per unit volume is large, whereby the amount of gas to be reacted can be increased, and the productivity will be improved. When the packed density of the catalyst-supporting carrier is at most 1 g/cm$^3$, the excessive temperature rise of the catalyst layer due to a heat of reaction can easily be controlled, and formation of byproducts can easily be suppressed.

In the reactor, there may be one or more portions packed with the catalyst-supporting carrier.

In order to carry out the gas phase reaction, the temperature of the catalyst layer is adjusted to be higher than the dew point of the raw material mixed gas comprising the raw material compound and hydrogen. Specifically, the temperature of the catalyst layer is preferably at least 50° C., since the boiling point of CFO-1214ya is 46° C. and the boiling point of HCFO-1224yd is assumed to be from 4 to 10° C., and in view of the reactivity, more preferably at least 60° C. from such a viewpoint that the conversion is thereby improved.

The temperature of the catalyst layer gradually decreases along with the progress of deterioration of the catalyst, thus leading to a problem that the conversion decreases. Therefore, it is preferred to carry out an operation to maintain the temperature of the catalyst layer at a sufficient temperature level so that the high conversion can be maintained. For example, in a case where the catalyst layer is heated from outside by e.g. a heating medium to maintain its temperature, it is possible to gradually increase the temperature of the heating medium thereby to increase the temperature of the catalyst layer.

Here, the temperature of the catalyst layer is the temperature of the catalyst layer which is maintained by heating from outside. Usually, the raw material mixed gas is reacted at a part of the region of the catalyst layer, and a reaction zone (the region where the raw material mixed gas is reacted) becomes a higher temperature than other regions of the catalyst layer, by generation of heat of reaction. The catalytic activity in this reaction zone will decrease as time passes, and usually, the reaction zone gradually moves from the inlet of the raw material mixed gas to the downstream side in the gas flow direction. Further, on the downstream side of the reaction zone, formed gas having a high temperature, formed in the reaction zone, flows and usually the temperature becomes higher than the temperature of the catalyst layer, and the temperature gradually decreases as apart from the reaction zone. In the present invention, the temperature of the catalyst layer is the temperature on the upstream side of the reaction zone i.e. the temperature of the catalyst layer, of which the temperature is maintained by heating from outside by e.g. a heating medium.

As mentioned above, in the reaction zone where the raw material mixed gas is reacted and in the region on the downstream side thereof, the temperature becomes higher than the temperature of the catalyst layer in other regions, due to the heat of reaction. By an excessive temperature rise of the catalyst layer due to the heat of reaction, 3,3,3-trifluoropropene ($CF_3CH=CH_2$, HFO-1243zf) will be formed as a byproduct. Therefore, it is preferred to maintain the maximum temperature of the catalyst layer to be low during the reaction so that the maximum temperature of the catalyst layer will not be too high. The maximum temperature of the catalyst layer during the reaction means the maximum temperature in a region of the catalyst layer where the temperature becomes higher than other regions due to the generation of the heat of reaction.

The maximum temperature of the catalyst layer during the reaction is at most 130° C., preferably at most 120° C., more preferably at most 100° C.

The maximum temperature of the catalyst layer during the reaction is measured as follows.

At the initial stage of the operation of the reactor, the catalyst in the vicinity of the gas inlet side of the catalyst layer contributes to the reaction, and as the operation of the reactor is continued and the catalyst deteriorates, the catalyst on the gas outlet side thereof tends to contribute to the reaction. In such a manner, as the operation of the reactor is continued, the reaction zone in the catalyst layer gradually moves from the gas inlet side towards the gas outlet side. That is, the portion showing the maximum temperature of the catalyst layer moves along with the movement of the reaction zone. Accordingly, at the initial stage of the operation of the reactor, the measuring portion of the insertion-type thermometer is positioned at the gas inlet side of the catalyst layer, and along with the progress of the reaction, the measuring portion is moved towards the gas outlet side to measure the maximum temperature of the catalyst layer.

As a method to maintain the maximum temperature of the catalyst layer to be at most 130° C., the following method ($\alpha$), method ($\beta$) or method ($\gamma$) may be mentioned, and from such a viewpoint that the productivity can be made high while maintaining the maximum temperature of the catalyst layer to be low, it is preferred to use the method ($\alpha$) alone, or the methods ($\alpha$) and ($\beta$) in combination, and it is more preferred to use the methods ($\alpha$) and ($\beta$) in combination. Further, with a view to suppressing formation of byproducts which are hardly separable from HFO-1234yf, it is preferred to use the method ($\alpha$) and/or the method ($\beta$) and the method ($\gamma$), in combination.

($\alpha$) A method of introducing the hydrogen gas from plural portions to the catalyst layer.

($\beta$) A method of using the raw material mixed gas containing an inert gas to lower the concentration of the raw material compound gas and hydrogen gas in the raw material mixed gas.

($\gamma$) A method of adjusting the temperature of the catalyst layer to be lower than the above-mentioned 50° C.

Method ($\alpha$):

By introducing the hydrogen gas from plural portions to the catalyst layer, the reaction zones of the raw material compound and the hydrogen in the catalyst layer can be dispersed without changing the introduced amount of the raw material compound, whereby generation of the heat of reaction is not localized at one portion. Therefore, it is possible to suppress local excessive heat generation in the catalyst layer and to easily maintain the maximum temperature of the catalyst layer to be at most 130° C., without lowering the productivity.

For example, the raw material mixed gas comprising the total amount of the raw material compound and a part of hydrogen to be used for the reaction, is introduced from the gas inlet side of the catalyst layer, and the rest of hydrogen is introduced from an intermediate portion of the catalyst layer, whereby a reaction zone (the first reaction zone) where the hydrogen and the raw material compound are reacted is formed in the catalyst layer on the inlet side of the hydrogen-introduction portion, and the hydrogen introduced from the hydrogen-introduction portion is mixed with the formed gas formed in the reaction zone (containing an unreacted raw material compound), so that a second reaction zone where the hydrogen and the raw material compound are reacted, will be formed in the catalyst layer on the outlet side of the hydrogen-introduction portion. By dispersing the reaction zones into two in the catalyst layer in such a manner, it is possible to suppress local excessive heat generation in the catalyst layer.

In the case of divided introduction of hydrogen, the number of the hydrogen-introduction portions is at least two portions including the gas inlet of the catalyst layer. The upper limit in the number of hydrogen-introduction portions is not particularly limited, but in order to avoid cumbersomeness, the number is preferably at most 5. Further, the amount of hydrogen to be introduced to each hydrogen-introduction portion is preferably substantially equal.

For example, in a case where there are at least two portions packed with the catalyst-supporting active carbon in the reactor, a part of hydrogen is introduced together with the raw material compound from the gas inlet side of the first stage packed portion, and the rest of hydrogen is introduced to the second and subsequent stage packed portions.

Method ($\beta$):

By using an inert gas to adjust the concentration of the raw material compound gas and hydrogen gas in the raw material mixed gas flowing in the catalyst layer and to lower the concentration of the raw material compound gas and hydrogen gas in the raw material mixed gas, it is possible to suppress an excessive temperature rise of the catalyst layer due to the heat of reaction. Further, it is possible to use a diluting gas other than an inert gas instead of the inert gas or together with the inert gas.

As the inert gas, nitrogen gas, rare gases, chlorofluorocarbons inert to the hydrogenation reaction, etc. may be mentioned. As the diluting gas other than an inert gas, hydrogen chloride may, for example, be mentioned.

The amount of the inert gas to be introduced is preferably at least 0.1 mol, more preferably at least 0.5 mol, per 1 mol of the raw material compound gas from such a viewpoint that it is easy to maintain the maximum temperature of the catalyst layer to be low, to suppress formation of byproduct and to suppress deterioration of the catalyst. Further, the amount of the inert gas to be introduced is preferably at most 10 mol, more preferably at most 4 mol, per 1 mol of the raw material compound gas from the viewpoint of the recovery rate of the inert gas.

Method ($\gamma$):

The temperature of the catalyst layer is made lower than the above-mentioned level, since the temperature of the reaction zone being lower is advantageous in order to suppress formation of byproducts which are hardly separable from HFO-1234yf and since in a reaction where the raw material is in a liquefied state, formation of byproducts having HFO-1234yf excessively reduced will increase thereby to lower the yield of HFO-1234yf. The temperature of the catalyst layer is preferably made to be higher than the dew point and lower than 50° C., more preferably higher than the dew point and at most 30° C. By adjusting the temperature of the catalyst layer to be lower, it becomes possible not only to suppress formation of byproducts but also to more readily remove the heat of reaction thereby to suppress an excessive temperature rise of the catalyst layer. In the method ($\gamma$), it is preferred to keep the temperature of the heating medium to heat the reactor to be low thereby to maintain the temperature of the catalyst layer at the above-mentioned level.

(Raw Material Compound)

The raw material compound is composed of at least one of CFO-1214ya and HCFO-1224yd.

CFO-1214ya:

As a method for producing CFO-1214ya, the following method may be mentioned.

A method of contacting 1,1-dichloro-2,2,3,3,3-pentafluoropropane ($CF_3CF_2CHCl_2$, HCFC-225ca) and an alkali aqueous solution in the presence of a phase-transfer catalyst for a dehydrofluorination reaction.

$$CF_3CF_2CHCl_2 \rightarrow CF_3CF=CCl_2 + HF \quad (3)$$

For the reaction of the formula (3), dichloropentafluoropropane (HCFC-225) including HCFC-225ca may be used, and only HCFC-225ca among the mixture of isomers is selectively dehydrofluorinated by the phase-transfer catalyst. After the reaction, CFO-1214ya is separated and recovered by a known method such as distillation.

HCFC-225 can be produced by reacting tetrafluoroethylene and dichlorofluoromethane in the presence of a catalyst such as aluminium chloride. HCFC-225 obtainable by such a reaction contains HCFC-225ca and 1,3-dichloro-1,2,2,3,3-pentafluoropropane ($CHClCF_2CClF_2$, HCFC-225cb) as the main components, and further contains a small amount of 2,2-dichloro-1,1,3,3,3-pentafluoropropane ($CHF_2CCl_2CF_3$, HCFC-225aa), 2,3-dichloro-1,1,2,3,3-pentafluoropropane ($CHF_2CClFCClF_2$, HCFC-225bb), etc.

As HCFC-225, a commercial product may be employed. As such a commercial product, ASAHIKLIN AK225 (manufactured by Asahi Glass Company, Limited, mixture of 48 mol % of HCFC-225ca and 52 mol % of HCFC-225cb) may, for example, be mentioned.

As the phase-transfer catalyst, tetrabutylammonium bromide (TBAB) is preferred.

HCFO-1224yd:

HCFO-1224yd is formed as an intermediate at the time of the reaction of the formula (1).

HCFO-1224yd recovered from the formed gas may be reacted together with CFO-1214ya as the raw material compound, with the hydrogen, or separately from CFO-1214ya, HCFO-1224yd may be reacted alone with the hydrogen.

(Introduction of Raw Material Mixed Gas)

The ratio of hydrogen to the raw material compound in the raw material mixed gas, as represented by the ratio of the number of moles of the hydrogen gas to the number of moles of chlorine atoms in the raw material compound ($H_2/Cl$) is preferably at most 0.7, more preferably at most 0.6, further preferably at most 0.5, from such a viewpoint that formation of byproducts can thereby be easily suppressed. Further, $H_2/Cl$ is preferably at least 0.1, more preferably at least 0.2, from the viewpoint of the yield of HFO-1234yf. Further, in a case where the hydrogen gas is dividedly introduced to the catalyst layer, the total amount of hydrogen to be introduced to the catalyst layer is the above amount of hydrogen.

The contact time of the raw material compound gas to the catalyst is preferably from 4 to 60 seconds, more preferably from 8 to 40 seconds. Such a contact time is a contact time of the raw material compound gas which is calculated from the volume of the catalyst layer and the amount of the gas to be introduced to the reactor.

The linear velocity u of the raw material compound gas represented by the following formula (I) in the catalyst layer, is preferably from 0.1 to 100 cm/sec., more preferably from 1 to 30 cm/sec. Such a linear velocity u is a linear velocity of the raw material compound gas which is calculated from the volume of the catalyst layer and the amount of the gas to be introduced to the reactor. When the linear velocity u of the raw material compound gas is at least 0.1 cm/sec, the productivity will be improved. When the linear velocity u of the raw material compound gas is at most 100 cm/sec, the conversion of the raw material compound gas and the hydrogen gas will be improved.

$$u = (W/100) \times V/S \quad (I)$$

In the formula (I), W is the concentration (mol %) of the raw material compound gas in the entire gas flowing through the catalyst layer, V is the flow rate ($cm^3$/sec) of the entire gas flowing through the catalyst layer, and S is the cross-sectional area ($cm^2$) of the catalyst layer to the flow direction of the gas.

(Formed Gas)

The formed gas contains, in addition to the desired product HFO-1234yf, an unreacted raw material compound gas, an intermediate (HCFO-1224yd), hydrogen chloride and byproducts (HFO-1243zf, 1,1,1,2-tetrafluoropropane ($CF_3CHFCH_3$, HFC-254eb), etc.).

In the above process (a), the formed gas is contacted with water, and in the above process (b), the formed gas is contacted with alkali at a temperature of at most 100° C.

<Process (a)>

In the process (a), hydrogen chloride contained in the formed gas is removed from the formed gas by contacting the formed gas discharged from the reactor with water to dissolve the hydrogen chloride in water. As mentioned above, since the reaction is carried out so that the maximum temperature of the catalyst layer is at most 130° C., the temperature of the formed gas at the formed gas outlet of the catalyst layer is at most 130° C. Accordingly, since no alkali is present, even if the formed gas at that temperature is contacted with water immediately after discharged from the reactor, a dehydrofluorination reaction of HFC-254eb contained as a byproduct in the formed gas will not take place, and there is no trouble of formation of HFO-1243zf. Here, the water is water which is not the after-mentioned alkali aqueous solution, and for example, even when it contains the after-mentioned metal hydroxide, the concentration of such a metal hydroxide is less than 0.01 mass %.

The method for contacting the formed gas with water may, for example, be a method of blowing the formed gas into water, or a method of contacting the formed gas with water sprayed from a scrubber.

(Recovery of HFO-1234yf)

As a method for recovering HFO-1243yf from the formed gas after the contact with water, a known method such as distillation may be mentioned.

(Functional Effects)

In the above-described process (a), the formed gas is contacted with water to remove hydrogen chloride contained in the formed gas, whereby a dehydrofluorination reaction of HFC-254eb contained as a byproduct in the formed gas does not take place, and at the time of removal of the hydrogen chloride, HFO-1243zf is not formed. Therefore, it is possible to obtain highly pure HFO-1234yf having the concentration of HFO-1243zf controlled to be low.

<Process (b)>

In the process (b), the formed gas discharged from the reactor is contacted with alkali at a temperature of at most 100° C. to neutralize hydrogen chloride and remove the hydrogen chloride from the formed gas.

By carrying out the reaction so that the maximum temperature of the catalyst layer becomes to be at most 130° C., as mentioned above, the temperature of the formed gas at the formed gas outlet of the catalyst layer is at most 130° C. In a case where the temperature of the formed gas is at most 100° C., even if the formed gas at that temperature is contacted with alkali immediately after discharged from the reactor, there is no substantial possibility that a dehydrofluorination reaction of HFC-254eb contained as a byproduct in the formed gas, will take place, and accordingly, there is no substantial possibility of formation of HFO-1243zf. In a case where the temperature of the formed gas exceeds 100° C., the formed gas of this temperature discharged from the reactor is cooled to at most 100° C. and then contacted with alkali.

The hydrogen chloride contained in the formed gas is removed from the formed gas by contacting the formed gas discharged from the reactor with alkali to neutralize the hydrogen chloride.

The method for contacting the formed gas with the alkali may, for example, be a method of blowing the formed gas into an alkali aqueous solution, or a method of contacting the formed gas with an alkali aqueous solution sprayed from a scrubber.

The alkali is preferably an alkali aqueous solution, whereby hydrogen chloride can efficiently be neutralized, and a formed salt can be dissolved and removed, and an aqueous solution of at least one metal hydroxide selected from the group consisting of sodium hydroxide, potassium hydroxide and calcium hydroxide, is more preferred, from the viewpoint of the availability of the alkali.

The concentration of the metal hydroxide is preferably from 0.01 to 40 mass % in the alkali aqueous solution (100 mass %). When the concentration of the metal hydroxide is at least 0.01 mass %, hydrogen chloride can efficiently be neutralized and removed. When the concentration of the metal hydroxide is at most 40 mass %, a dehydrofluorination reaction of HFC-254eb contained as a byproduct in the formed gas, can sufficiently be suppressed.

The temperature of the formed gas immediately before contacted with the alkali is at most 100° C., preferably at most 80° C., more preferably at most 50° C. When the temperature of the formed gas is at most 100° C., a dehydrofluorination reaction of HFC-254eb contained as a byproduct in the formed gas can sufficiently be suppressed. Even if the maximum temperature of the catalyst layer is close to 130° C., if there is a catalyst layer having a low temperature on the downstream side of the reaction zone showing the maximum temperature, the formed gas will be cooled at that portion, so that the temperature of the formed gas discharged from the reactor can be made to at most 100° C., and even if the temperature of the formed gas discharged from the reactor exceeds 100° C., it can be cooled to at most 100° C. before it is contacted with alkali.

The temperature of the formed gas immediately before contacted with the alkali is preferably at least 0° C., more preferably at least 10° C., with a view to suppressing an excess energy to cool the formed gas.

Further, when the formed gas is contacted with the alkali, the alkali will be heated by the heat of neutralization. The maximum temperature of the alkali thereby heated by the heat of neutralization is at most 100° C., preferably at most 80° C., more preferably at most 50° C.

The temperature of the alkali is preferably at least 0° C., more preferably at least 10° C. with a view to suppressing an excess energy to cool the alkali.

(Functional Effects)

In the above-described process (b), the formed gas is contacted with an alkali at a temperature of at most 100° C., to neutralize and remove hydrogen chloride contained in the formed gas, whereby a dehydrofluorination reaction of HFC-254eb contained as a byproduct in the formed gas is suppressed, and at the time of the removal of hydrogen chloride, HFO-1243zf is less likely to be formed. Therefore, it is possible to obtain highly pure HFO-1234yf having the concentration of HFO-1243zf controlled to be low.

EXAMPLES

Now, the present invention will be described in further detail with reference to Examples. However, it should be understood that the present invention is by no means restricted by the following description.

Examples 1 is a Preparation Example, Example 2 is a Working Example of the present invention, and Example 3 is a Comparative Example.

Example 1

Production of CFO-1214ya:

CFO-1214ya was produced by the following method by using, as a reaction raw material, HCFC-225 (ASAHIKLIN AK225 manufactured by Asahi Glass Company, Limited, HCFC-225ca: 48 mol %, HCFC-225cb: 52 mol %).

Into a glass reactor having an internal capacity of 1 L and provided with a Dimroth condenser cooled to 0° C., 3 g of TBAB as a phase-transfer catalyst, 83 g (1.485 mol) of potassium hydroxide, 180 g of water, and 609 g (3.0 mol) of ASAHIKLIN AK225 were charged and then gradually heated with stirring, and a reaction was carried out at 45° C. for one hour. Thereafter, the reaction crude liquid phase-separated into two phases of an organic phase and an aqueous phase, was subjected to liquid separation. The organic phase was charged into a distillation column having an oven capacity of 1 L and an ability of theoretical number of plates of 10 plates, and distillation was carried out. As a result of the distillation, 262 g (1.43 mol) of CFO-1214ya (boiling point: 45° C.) having a purity of 99.5%, was obtained.

Example 2

Production of HFO-1234yf:

For the production of HFO-1234yf, a reaction apparatus 101 shown in FIG. 1 was used.

The reaction apparatus 101 is provided with two reaction tubes 110A and 110B and a salt bath 130 for immersion of such reaction tubes. The reaction tube 110A has catalyst-packing portions 113a and 114a at two positions on the inlet 111a side and the outlet 112a side. Likewise, the reaction tube 110B has catalyst-packing portions 113b and 114b at two positions on the inlet 111b side and the outlet 112b side. The outlet 112a of the reaction tube 110A is connected by piping to the inlet 111b of the reaction tube 110B.

As the reaction tubes 110A and 110B, reaction tubes made of Inconel (registered trademark) 600 and having an inner diameter of 2.54 cm and a length of 100 cm, were used. Further, as the catalyst, palladium-supporting active carbon having 0.5 part by mass of palladium supported per 100 parts by mass of coconut shell active carbon, was used, and such a catalyst was packed in the catalyst-packing portion 114a on the outlet 112a side of the reaction tube 110A to form a catalyst layer 120A having a height of 40 cm. Likewise, the above catalyst was packed in the respective catalyst-packing portion 113b and 114b on the inlet 111b side and the outlet 112b side of the reaction tube 110B to form a catalyst layer 120B and a catalyst layer 120C each having a height of 40 cm. The packed density of the palladium-supporting active carbon in catalyst layers 120A to 120C was adjusted to be 0.73 g/cm$^3$.

Then, the reaction tube 110A and the reaction tube 110B were immersed in the salt bath 130 so that all of the catalyst layers 120A to 120C were immersed, and the catalyst layers 120A to 120C were heated to 80° C.

A raw material compound gas (A) composed of CFO-1214ya obtained in Example 1, hydrogen gas (B) and nitrogen gas (C) were permitted to flow through reaction tubes 110A and 110B in a molar ratio of the total introduced amounts being hydrogen/CFO-1214ya/nitrogen=1/1/2. The contact time of the raw material compound gas (A) to the catalyst layers 120A to 120C was adjusted to be 40 seconds, and the linear velocity u of the raw material compound gas (A) was adjusted to be 7 cm/sec.

Further, 50% of the hydrogen gas (B) was introduced from the inlet 111a of the reaction tube 110A together with the raw material compound gas (A), and the rest was introduced to the piping portion connecting the reaction tube 110A and the reaction tube 110B. That is, in the catalyst layer (catalyst layer length 120 cm) consisting of catalyst layers 120A to 120C, the hydrogen gas (B) was dividedly introduced at two portions i.e. the catalyst layer 120A (0 cm point) and the catalyst layer 120B (40 cm point).

The maximum temperature of the catalyst layers 120A to 120C during the reaction was measured by insertion-type thermometers 140A to 140C inserted respectively to such catalyst layers. The maximum temperature of the catalyst layers 120A to 120C was 90° C.

The formed gas discharged from the outlet 112b of the reaction tube 110B of the reaction apparatus 101 was analyzed by gas chromatography (GC), and the conversion ratio X from CFO-1214ya to HFO-1234yf was calculated by the following formula (II) and found to be 74%.

$$X=[Y/(Z/2)]\times 100 \tag{II}$$

wherein Y is the number of moles of the formed HFO-1234yf, and Z is the number of moles of the introduced CFO-1214ya.

Further, an unsaturated compound formed by a side reaction was only an intermediate (HCFO-1224yd), and the conversion ratio to HCFO-1224yd was calculated and found to be 20%.

The formed gas discharged from the outlet 112b of the reaction tube 110B of the reaction apparatus 101 was blown into a 20 mass % sodium hydroxide aqueous solution in a cleaning container 150. The temperature of the formed gas immediately before blown into the sodium hydroxide aqueous solution was 20° C. Further, the maximum temperature of the sodium hydroxide aqueous solution in the vicinity of the inlet of the blown formed gas was 22° C.

The formed gas (D) discharged from the cleaning container 150 was analyzed by GC, whereby an unsaturated compound other than HFO-1234yf and HCFO-1224yd was not detected.

The formed gas (D) was collected in a trap cooled by dry ice and then purified by distillation, whereby HFO-1234yf having a purity of at least 99.9 mol % was obtained, and by the analysis by GC, an unsaturated compound other than HFO-1234yf was not detected.

Example 3

Formed gas (D) was obtained in the same manner as in Example 2 except that 100% of the hydrogen gas (B) was introduced together with the raw material compound gas (A) from the inlet 111a of the reaction tube 110A.

The maximum temperature of the catalyst layers 120A to 120C was 180° C.

The temperature of the formed gas immediately before blown into the sodium hydroxide aqueous solution was 105° C. Further, the maximum temperature of the sodium hydroxide aqueous solution in the vicinity of the inlet of the blown formed gas was 100° C.

The formed gas discharged from the outlet 112b of the reaction tube 110B of the reaction apparatus 101 was analyzed by GC, and the conversion ratio X to HFO-1234yf was calculated and found to be 74%. Further, as unsaturated compounds formed by side-reactions, an intermediate (HCFO-1224yd, conversion ratio=20%) and 1,500 volume ppm of HFO-1243zf were detected.

The formed gas (D) discharged from the cleaning container 150 was analyzed by GC, whereby in addition to HFO-1234yf and HCFO-1224yd, 2,700 volume ppm of HFO-1243zf was detected.

The formed gas (D) was collected in a trap cooled by dry ice and then purified by distillation, whereby HFO-1234yf having a purity of at least 99.9 mol % was obtained, but by the analysis by GC, in addition to HFO-1234yf, 730 volume ppm of HFO-1243zf was detected.

INDUSTRIAL APPLICABILITY

HFO-1234yf obtained by the process of the present invention is useful as a new refrigerant which is less influential to the environment.

The entire disclosures of Japanese Patent Application No. 2010-142669 filed on Jun. 23, 2010 and U.S. Provisional Patent Application No. 61/365,582 filed on Jul. 19, 2010 including specifications, claims, drawings and summaries are incorporated herein by reference in their entireties.

REFERENCE SYMBOLS

110A: Reaction tube (Reactor)
110B: Reaction tube (Reactor)
120A: Catalyst layer
120B: Catalyst layer
120C: Catalyst layer
A: Raw material compound gas
B: Hydrogen gas
D: Formed gas

What is claimed is:

1. A process for producing 2,3,3,3-tetrafluoropropene, which comprises reacting a raw material compound composed of 1,1-dichloro-2,3,3,3-tetrafluoropropene and/or 1-chloro-2,3,3,3-tetrafluoropropene, and hydrogen in a gas phase in a reactor having a catalyst layer packed with a catalyst-supporting carrier, while maintaining the maximum temperature of the catalyst layer to be at most 130° C., to obtain formed gas containing 2,3,3,3-tetrafluoropropene, and then, contacting the formed gas discharged from the reactor, with water.

2. A process for producing 2,3,3,3-tetrafluoropropene, which comprises reacting a raw material compound composed of 1,1-dichloro-2,3,3,3-tetrafluoropropene and/or 1-chloro-2,3,3,3-tetrafluoropropene, and hydrogen in a gas phase in a reactor having a catalyst layer packed with a catalyst-supporting carrier, while maintaining the maximum temperature of the catalyst layer to be at most 130° C., to obtain formed gas containing 2,3,3,3-tetrafluoropropene, and then, contacting the formed gas discharged from the reactor, with alkali, while adjusting the temperature of the formed gas to be at most 100° C. immediately before the contact with alkali.

3. The process for producing 2,3,3,3-tetrafluoropropene according to claim 2, wherein the alkali is an alkali aqueous solution.

4. The process for producing 2,3,3,3-tetrafluoropropene according to claim 3, wherein the alkali aqueous solution is an aqueous solution of at least one metal hydroxide selected from the group consisting of sodium hydroxide, potassium hydroxide and calcium hydroxide.

5. The process for producing 2,3,3,3-tetrafluoropropene according to claim 4, wherein the concentration of the metal hydroxide is from 0.01 to 40 mass % in the alkali aqueous solution (100 mass %).

6. The process for producing 2,3,3,3-tetrafluoropropene according to any one of claims 1 to 5, wherein the catalyst is palladium.

7. The process for producing 2,3,3,3-tetrafluoropropene according to claim 1 or 2, wherein the carrier is active carbon.

8. The process for producing 2,3,3,3-tetrafluoropropene according to claim 1 or 2, wherein the packed density of the catalyst-supporting carrier in the catalyst layer is from 0.5 to 1 $g/cm^3$.

9. The process for producing 2,3,3,3-tetrafluoropropene according to claim 1 or 2, wherein the catalyst is palladium or a palladium alloy.

10. The process for producing 2,3,3,3-tetrafluoropropene according to claim 1 or 2, wherein the catalyst comprises a mixture of palladium with another metal.

11. The process for producing 2,3,3,3-tetrafluoropropene according to claim 1 or 2, wherein the catalyst comprises palladium.

12. The method for producing 2,3,3,3-tetrafluoropropene according to claim 1 or 2, wherein the catalyst comprises palladium and the catalyst is supported on a carrier.

13. The method for producing 2,3,3,3-tetrafluoropropene according to claim 1 or 2, wherein the isolated 2,3,3,3-tetrafluoropropene has a purity of 99.5 to 99.9 mol %.

14. The method for producing 2,3,3,3-tetrafluoropropene according to claim 1 or 2, further comprising isolating the 2,3,3,3-tetrafluoropropene and wherein the isolated 2,3,3,3-tetrafluoropropene has a purity of 99.5 to 99.9 mol %.

* * * * *